United States Patent

Maekawa et al.

Patent Number: 5,455,347
Date of Patent: Oct. 3, 1995

[54] PIPERIDINE COMPOUNDS

[75] Inventors: Kazuo Maekawa; Yutaka Nakahara; Kouzaburo Shinpo, all of Saitama, Japan

[73] Assignee: Asahi Denka Kogyo Kabushiki Kaisha, Tokyo, Japan

[21] Appl. No.: 154,000

[22] Filed: Nov. 18, 1993

[51] Int. Cl.⁶ ................................................ C07D 403/14
[52] U.S. Cl. ................................................................ 544/198
[58] Field of Search ............................................. 544/198

[56] References Cited

FOREIGN PATENT DOCUMENTS

| | | |
|---|---|---|
| 0399953 | 11/1990 | European Pat. Off. |
| 0468928 | 1/1992 | European Pat. Off. |
| 61-176662 | 8/1986 | Japan |

Primary Examiner—Yogendra N. Gupta
Attorney, Agent, or Firm—Young & Thompson

[57] ABSTRACT

A piperidine compound represented by the following general formula (I) and a stabilized polymeric material composition containing said compound.

$$A[(O-X)_n NH-Y]_m \quad (I)$$

(wherein A represents a residue formed by eliminating m hydroxyl groups from a polyhydric (tri- to hexa-hydric) alcohol; X represents an alkylene group having 2 to 4 carbon atoms; n is an integer of from 1 to 15; m is an integer of from 3 to 6; and Y represents a group:

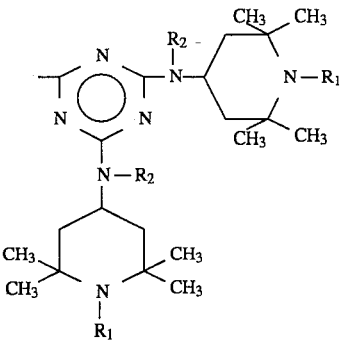

wherein $R_1$ represents a hydrogen atom, an alkyl, alkoxy or acyl group having 1 to 18 carbon atoms or an oxygen free radical; and $R_2$ represents a hydrogen atom or an alkyl group having 1 to 18 carbon atoms.)

5 Claims, No Drawings

PIPERIDINE COMPOUNDS

BACKGROUND OF THE INVENTION

1. Field of the Invention

This invention relates to a piperidine compound and a stabilized polymeric material composition containing said compound. More particularly, it relates to a specific cyanurate derivative having a 2,2,6,6-tetramethylpiperidyl group and a stabilized polymeric material composition which has been improved particularly in heat resistance, non-extractibility and light resistance by incorporating said derivative therein.

2. Description of the Prior Art

It is known that polymeric materials such as polyethylene, polypropylene and polyvinyl chloride are generally susceptible to light and suffer from, for example, degradation, color changes or deterioration in mechanical strength due to the action of light, which makes them unable to withstand prolonged use.

Accordingly, there have been employed various stabilizers in order to protect these polymeric materials from deterioration caused by light and it has been proposed to use a number of compounds having a 2,2,6,6-tetramethylpiperidyl group in its molecule for this purpose.

Among these piperidine compounds, cyanurate derivatives are relatively excellent in the heat resistance of the compounds per se and thus it has been proposed to use several of these compounds hitherto. For example, Japanese Patent Laid-Open No. 21389/1974 has proposed to use cyanurate derivatives of piperidine compounds. However, the compounds described in this patent are low-molecular weight ones and thus have several disadvantages such that they are liable to be vaporized during the processing of polymeric materials or easily extracted with water or organic solvents.

To solve this problem, high-molecular weight compounds have been proposed by, for example, Japanese Patent Laid-Open No. 73886/1977, No. 47030/1983, No. 194931/1983, No. 122487/1984 and No. 81441/1986. Further, Japanese Patent Laid-Open No. 176662/1986 has proposed to use a cyanurate derivative of a diamine having an ether group in its molecule. However, these compounds are still insufficient in stabilizing effect and cannot be satisfactorily used in practice.

SUMMARY OF THE INVENTION

Under these circumstances, the present inventors have conducted extensive studies and consequently found out that a stabilized polymeric material composition being excellent in heat resistance, non-extractibility and light resistance can be obtained by adding a specific cyanurate derivative having an ether bond, thus completing the present invention.

Accordingly, the present invention provides a piperidine compound represented by the following general formula (I).

The present invention further provides a stabilized polymeric material composition obtained by adding 0.001 to 5 parts by weight of at least one piperidine compound represented by the following general formula (I) to 100 parts by weight of a polymeric material.

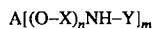
(I)

(wherein A represents a residue formed by eliminating m hydroxyl groups from a polyhydric (tri- to hexa-hydric) alcohol; X represents an alkylene group having 2 to 4 carbon atoms; n is an integer of from 1 to 15; m is an integer of from 3 to 6; and Y represents a group:

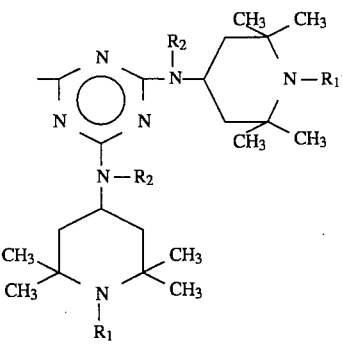

wherein $R_1$ represents a hydrogen atom, an alkyl, alkoxy or acyl group having 1 to 18 carbon atoms or an oxygen free radical; and $R_2$ represents a hydrogen atom or an alkyl group having 1 to 18 carbon atoms.)

The polymeric material composition of the present invention containing the piperidine compound of the present invention represented by the above general formula (I) is one being exhibiting excellent heat resistance, non-extractibility and light resistance.

DETAILED DESCRIPTION OF THE INVENTION

Now, the piperidine compound and the polymeric material composition containing said compound according to the present invention will be described in greater detail.

As examples of the polyhydric (tri- to hexa-hydric) alcohol residue represented by A in the above general formula (I), residues of glycerol, trimethylolethane, trimethylolpropane, tris(2-hydroxyethyl) isocyanurate, pentaerythritol, diglycerol, ditrimethylolethane, ditrimethylolpropane, mannitol, sorbitol, dipentaerythritol and inositol may be cited.

As the piperidine compound of the present invention represented by the above general formula (I), those wherein the polyhydric alcohol residue represented by A is a group having a neopentyl structure represented by the following formula are particularly preferable because of the large effects thereof.

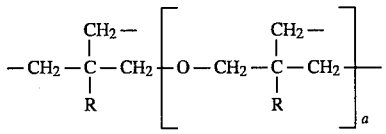

(wherein R represents an alkyl group having 1 to 18 carbon atoms or —CH$_2$—; and a is 0 or 1.)

As examples of the alkyl groups represented by $R_1$ and $R_2$ in the above general formula (I), unsubstituted alkyl groups such as methyl, ethyl, propyl, isopropyl, butyl, isobutyl, pentyl, hexyl, octyl, 2-ethylhexyl, decyl, dodecyl, tridecyl, tetradecyl and octadecyl groups and substituted alkyl groups such as benzyl, phenylethyl, 2-hydroxyethyl, 2,3-epoxypropyl, dimethylaminopropyl and methoxyethyl groups may be cited. As examples of the alkoxy group represented by $R_1$, alkoxy groups derived from the above-mentioned alkyl groups may be cited. As examples of the acyl group represented by $R_1$, acetyl, propionyl, acryloyl, methacryloyl, butyroyl and octanoyl groups may be cited.

As example of the alkylene group represented by X in the above general formula (I), ethylene, propylene, trimethylene, butylene, isobutylene and tetramethylene groups may be cited.

The piperidine compound of the present invention represented by the above general formula (I) can be easily prepared by, for example, reacting cyanuric chloride with a 4-piperidylamine compound to give 2-chloro-4,6-bis(polyalkylpiperidin-4-yl)triazine, alkylating or acylating the piperidyl group at the 1-position if necessary, and then reacting the obtained product with a polyamine compound represented by the following general formula (II):

$$A[(O-X)_n NH_2]_m \qquad (II).$$

The polyamine compound represented by the above general formula (II) can be prepared in accordance with a conventional method comprising, for example, adding an alkylene oxide to a polyhydric (tri- to hexa-hydric) alcohol represented by $A(OH)_m$ and then aminating the terminal hydroxyl groups. Those which are commonly marketed may be used as such therefor. In the above general formula (II), n represents the average addition mole number of the alkylene oxide and the mole numbers of the alkylene oxide added to the hydroxyl groups of the polyhydric alcohol may be either the same or different from each other.

Next, typical examples (compounds No. 1 to No. 6) of the piperidine compound of the present invention represented by the above general formula (I) to be used in the polymeric material composition of the present invention will be shown. In the following compounds No. 1 to No. 6 and the comparative compounds as will be given in Examples hereinafter, $B_1$ to $B_4$ respectively represent the groups shown in the following Formula 1. In practice, the compounds No. 1 to No. 6 are each in the form of a mixture of two or more compounds differing in n in the above general formula (I) from each other and p, q, r and s in Formula 1 each represents the average of n of two or more compounds constituting said mixture. [Formula 1]

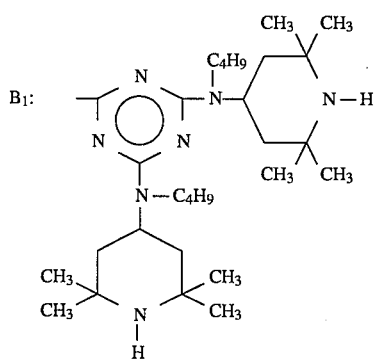

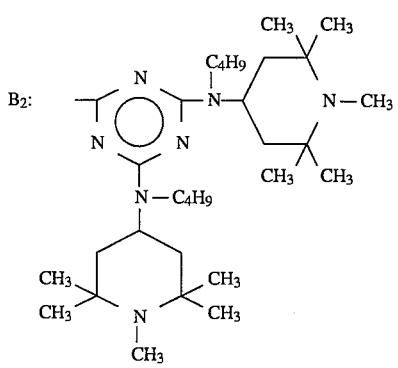

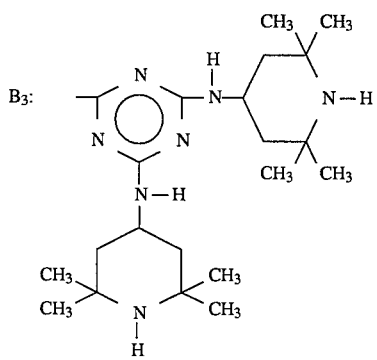

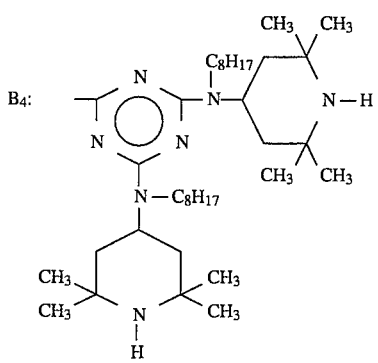

Compound No. 1

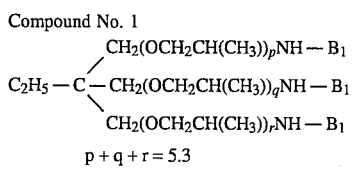

$p + q + r = 5.3$

Compound No. 2

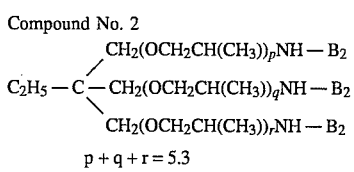

$p + q + r = 5.3$

-continued

Compound No. 3
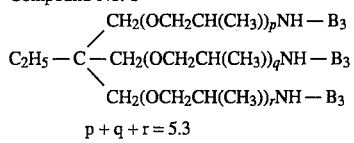
$p + q + r = 5.3$

Compound No. 4
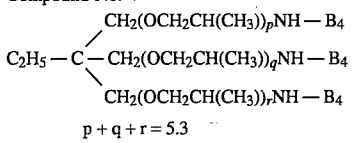
$p + q + r = 5.3$

Compound No. 5
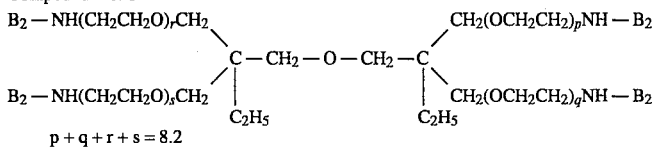
$p + q + r + s = 8.2$

Compound No. 6
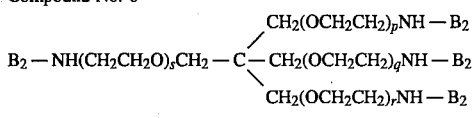
$p + q + r + s = 16.9$

To further illustrate a method for synthesizing the piperidine compound represented by the above general formula (I) to be used in the present invention, the following Synthesis Example will be given. However, it is to be understood that the present invention is not restricted to the following synthesis method.

(Synthesis Example) Synthesis of compound No. 2:

(1) Preparation of 2-chloro-(4,6-bis [N-(2,2,6,6-tetramethylpiperidin-4-yl)-N-butylamino]) triazine 28.2 g of cyanuric chloride was dissolved in 230 g of xylene at a temperature of 20° to 30° C. Then 64.4 g of N-butyl-N-(2,2,6,6-tetramethyl-4-piperidyl)amine was dropped into the solution obtained above under stirring at a temperature of 65° C. or below over 1 hour. Further, 57.8 g of 25% sodium hydroxide was dropped thereinto over 30 minutes. After the completion of the addition, the mixture was reacted at 65° C. for additional 5 hours. Next, the reaction mixture was separated into an oily phase and an aqueous phase and washed with water.

(2) N-methylation

87% of paraformaldehyde was added to the above-mentioned reaction mixture. After heating to 80° C., 23.3 g of an 80% aqueous solution of formic acid was dropped thereinto over 1 hour. After reacting at 90° C. for additional 5 hours, the reaction mixture was neutralized by adding 31.6 g of a 40% aqueous solution of sodium hydroxide, divided into an oily phase and an aqueous phase, washed with water, dehydrated and filtered.

(3) Preparation of compound No. 2

To the filtrate as obtained above were added 22 g of [ω-aminopoly(propyloxy)methyl]propane (Jeffamine T-403, p+q+r=5.3; mfd. by Mitsui Texaco Chemical) and 20 g of sodium hydroxide. The obtained mixture was reacted by refluxing with xylene under nitrogen atmosphere for 18 hours, subsequently washed with water, dehydrated and filtered. After solvent removal, a product in the form of a glassy solid with a softening point of 85° to 95° C. was obtained (yield: 96.5%).

The product thus obtained was analyzed by high performance liquid chromatography. The result revealed that it showed a single peak and had a molecular weight of about 2,000 (calculated value: 2021.8). The data of elemental analysis on this product well agreed with the calculated data, as shown below. Thus it was confirmed that this product was the target compound.

Elemental analysis data:

|  | C | H | N |
|---|---|---|---|
| found (%): | 72.4 | 12.9 | 11.0 |
| calcd. (%): | 71.9 | 12.5 | 11.2. |

Examples of the polymeric material to be improved in the stability in accordance with the present invention include α-olefin homopolymers and copolymers such as high-density, low-density or linear and low-density polyethylene, polypropylene, polybutene-1, poly-3-methylpentene and ethylene/propylene copolymer, poly-unsaturated compounds of these α-olefins with conjugated or unconjugated dienes, copolymers with acrylic acid, methacrylic acid and vinyl acetate, halogen-containing resins such as polyvinyl chloride, polyvinylidene chloride, chlorinated polyethylene, chlorinated polypropylene, polyvinylidene fluoride, chlorinated rubber, vinyl chloride/vinyl acetate copolymer, vinyl chloride/ethylene copolymer, vinyl chloride/vinylidene chloride copolymer, vinyl chloride/vinylidene chloride/vinyl acetate terpolymer, vinyl chloride/acrylate copolymer, vinyl chloride/maleate copolymer and vinyl chloride/cyclohexylmaleimide copolymer, thermoplastic synthetic resins such as petroleum resin, coumarone resin, polystyrene, polyvinyl acetate, acrylic resin, copolymers of styrene and/or α-methylstyrene with other monomers (for example, maleic anhydride, phenylmaleimide, methyl methacrylate, butadiene and acrylonitrile) such as AS resin, ABS resin, MBS resin and heat-resistant ABS resin, linear polyesters such as polymethyl methacrylate, polyvinyl alcohol, polyvinyl formal, polyvinyl butyral, polyethylene terephthalate and polytetramethylene terephthalate, polyamides such as polyphenylene oxide, polycaprolactam and polyhexamethyleneadipamide, polycarbonate, polyacetal, polyphenylene sulfide, polyurethane and cellulosic resin, thermosetting resins such as phenol resin, urea resin, melamine resin, epoxy resin and unsaturated polyester resin as well as elastomers, for example, isoprene rubber, butadiene rubber, acrylonitrile/butadiene copolymer rubber, styrene/butadiene copolymer rubber and copolymer rubbers with α-olefins such as ethylene, propylene and butene-1 and terpolymers of ethylene, α-olefin and unconjugated dienes such as ethylidenenorbornene and cyclopentadiene. Also, blends of these resins and/or elastomers are usable therefor.

To 100 parts by weight of the polymeric material is added the piperidine compound of the present invention represented by the above general formula (I) in an amount of from 0.001 to 5 parts by weight, preferably from 0.01 to 3 parts by weight.

Together with the piperidine compound of the present invention represented by the above general formula (I), the polymeric material composition according to the present invention may contain other additives commonly employed in the art, for example, antioxidants, UV absorbers, hindered-amine light stabilizers other than the piperidine compound represented by the above general formula (I) and stabilizers.

Particularly preferable examples of the above-mentioned additives include phenol-, phosphorus- and sulfur-based antioxidants and UV absorbers.

Examples of the phenol-based antioxidants as described above include 2,6-di-tert-butyl-p-cresol, 2,6-diphenyl-4-octadecyloxyphenol, stearyl (3,5-di-tert-butyl-4-hydroxyphenyl) propionate, distearyl (3,5-di-tert-butyl-4-hydroxybenzyl) phosphonate, thiodiethylene glycol bis[(3,5-di-tert-butyl-4hydroxyphenyl)propionate], 1,6-hexamethylenebis-[(3,5-di-tert-butyl-4-hydroxyphenyl)propionate], 1,6-hexamethylenebis[(3,5-di-tert-butyl-4hydroxyphenyl)propionamide], 4,4'-thiobis(6-tert-butyl-m-cresol), 2,2'-methylenebis(4-methyl-6-tertbutylphenol), 2,2'-methylenebis(4-ethyl-6-tert-butylphenol), bis[3,3-bis(4-hydroxy-3-tert-butylphenyl)butyric acid] glycol ester, 4,4'-butylidenebis(6-tert-butyl-m-cresol), 2,2'-ethylidenebis(4,6-di-tert-butyl-phenol), 2,2'-ethylidenebis(4-sec-butyl-6-tertbutylphenol), 1,1,3-tris(2-methyl-4-hydroxy-5-tertbutylphenyl)butane, bis[2-tert-butyl-4-methyl-6(2-hydroxy-3-tert-butyl-5-methylbenzyl) phenyl] terephthalate, 1,3,5-tris(2,6-dimethyl-3-hydroxy-4-tert-butylbenzyl) isocyanurate, 1,3,5-tris(3,5-di-tert-butyl-4-hydroxybenzyl) isocyanurate, 1,3,5-tris(3, 5-di-tert-butyl-4-hydroxybenzyl)-2,4,6-trimethylbenzene, 1,3,5-tris[(3,5-di-tert-butyl-4-hydroxyphenyl)propionyloxyethyl] isocyanurate, tetrakis[methylene-3-(3,5-di-tert-butyl-4-hydroxyphenyl)propionate] methane, 2-tert-butyl-4-methyl-6(2-acryloyloxy-3-tert-butyl-5-methylbenzyl) phenol, 3,9-bis[1,1-dimethyl-2-{(3-tert-butyl-4-hydroxy-5methylphenyl)propionyloxy}ethyl]-2,4, 8,10-tetraoxaspiro[5.5]undecane and triethylene glycol bis[(3-tert-but-1-4-hydroxy-5-methylphenyl) propionate].

Examples of the phosphorus-based antioxidants as described above include tris(nonylphenyl) phosphite, tris-(mono- and di-mixed nonylphenyl) phosphite, tris(2,4-di-tert-butylphenyl) phosphite, tris [2-tert-butyl-4-(3-tert-butyl-4-hydroxy-5-methylphenylthio)-5-methylphenyl] phosphite, tri(tridecyl) phosphite, octyl diphenyl phosphite, di(tridecyl) pentaerythritol diphosphite, distearyl pentaerythritol diphosphite, di(nonylphenyl) pentaerythritol diphosphite, bis(2,4-di-tert-butylphenyl) pentaerythritol diphosphite, bis(2,6-di-tert-butyl-4-methylphenyl) pentaerythritol diphosphite, bis(2,4,6-tri-tertbutylphenyl) pentaerythritol diphosphite, tetra(tridecyl) isopropylidenediphenol diphosphite, tetra(tridecyl)-4,4'-n-butylidenebis(2-tertbutyl-5-methylphenol) diphosphite, hexa(tridecyl)-1,1,3-tris (2-methyl-4-hydroxy-5-tert-butylphenyl)butane triphosphite, 2,2'-methylenebis(4,6-di-tertbutylphenyl) octyl phosphite, 2,2'-methylenebis(4,6-di-tert-butylphenyl) fluorophosphite, tetrakis(2,4-di-tert-butylphenyl) biphenylenediphosphonite and 9-phospha-10-oxaphenanthrene 9-oxide.

Examples of the sulfur-based antioxidants as described above include dialkyl thiodipropionates such as dilauryl, dimyristyl and distearyl thiodipropionates and β-alkylmercaptopropionates of polyols such as pentaerythritol tetra(β-dodecylmercaptopropionate).

Examples of the above-mentioned UV absorbers include 2-hydroxybenzophenones such as 2,4-dihydroxybenzophenone, 2-hydroxy-4-methoxybenzophenone, 2-hydroxy-4-octoxybenzophenone and 5,5=-methylenebis(2-hydroxy-4-methoxybenzophenone); 2-(2'-hydroxyphenyl)benzotriazoles such as 2-(2'-hydroxy-5'-methylphenyl)benzotriazole, 2-(2'-hydroxy-3',5'-di-tert-butylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tertoctylphenyl)benzotriazole, 2-(2'-hydroxy-3', 5'-dicumylphenyl)benzotriazole and 2,2'-methylenebis(4-tert-octyl-6-benzotriazole) phenol; benzoates such as phenyl salicylate, resorcinol monobenzoate, 2,4-di-tert-butylphenyl 3',5'-di-tert-butyl-4'-hydroxybenzoate and hexadecyl 3,5-di-tert-butyl-4-hydroxybenzoate; substituted oxanilides such as 2-ethyl-2'-ethoxyanilide and 2-ethoxy-4'-dodecyloxanilide; and cyanoacrylates such as ethyl α-cyano-β,β-diphenylacrylate and methyl 2-cyano-3-methyl-3-(p-methoxyphenyl) acrylate.

If necessary, the polymeric material composition of the present invention may further contain, for example, heavy metal inactivators, nucleating agents, metallic soaps, organotin compounds, plasticizers, epoxy compounds, foaming agents, antistatic agents, flame-retardants, lubricants and processing aids.

The polymeric material composition according to the present invention can be appropriately used for purposes where a high weatherability is required for a prolonged period of time, for example, agricultural materials, automobile paints and interior and exterior materials. It is applicable to, for example, films, fibers, tapes, sheets, various molding materials, paints, lacquer binders, adhesives, putties and bases for photographic materials.

To illustrate the stabilizing effect of the polymeric material composition of the present invention, the following Examples will be given. However, it is to be understood that the present invention is not restricted thereto.

EXAMPLE 1

In accordance with the composition as specified below, a pressed sheet of 0.3 mm in thickness was formed. Then the sheet thus formed was subjected to a light-resistance test by using a high-pressure mercury pump (the data thus obtained are referred to as "original" in Table 1). Further another sheet, which had been irradiated with light for 100 hours and then immersed in hot water at 80° C. for 24 hours, was also subjected to the light-resistance test (the data thus obtained are referred to as "immersed in hot water" in Table 1). Table 1 summarizes the results.

| [Composition] | part by weight |
|---|---|
| polypropylene | 100 |
| pentaerythritol tetrakis(3,5-di-tert-butyl-4-hydroxyphenyl- | 0.1 |

| [Composition] | part by weight |
|---|---|
| propionate) | |
| calcium stearate | 0.05 |
| test compound (see Table 1) | 0.1 |

TABLE 1

| No. | Test compound | Light resistance (hr) Original | Immersed in hot water |
|---|---|---|---|
| Comp. Ex. 1-1 | comp. cmpd. H-1 | 560$^{Hr}$ | 420$^{Hr}$ |
| Comp. Ex. 1-2 | comp. cmpd. H-2 | 590 | 410 |
| Ex. 1-1 | cmpd. No. 1 | 760 | 690 |
| Ex. 1-2 | cmpd. No. 2 | 770 | 690 |
| Ex. 1-3 | cmpd. No. 3 | 750 | 670 |
| Ex. 1-4 | cmpd. No. 4 | 760 | 680 |
| Ex. 1-5 | cmpd. No. 5 | 740 | 670 |
| Ex. 1-6 | cmpd. No. 6 | 750 | 680 |

The comparative compounds given in the above table are those represented by the following formulae respectively wherein $B_1$ is a group represented by the above Formula 1.

Comparative compound H-1:

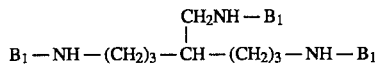

Comparative compound H-2:

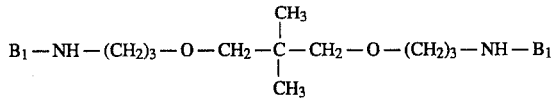

EXAMPLE 2

In accordance with the composition as specified below, materials were mixed in a mixer for 5 minutes and formulated into a compound with the use of an extruder at cylinder temperatures of 230° and 240° C., a head dice temperature of 250° C. and a rotational speed of 20 rpm. Next, the compound was treated at a cylinder temperature of 240° C. and a nozzle temperature of 250° C. under an injection pressure of 475 kg/cm² to thereby give a test piece.

Further, a compound which had been repeatedly subjected to the above-mentioned extrusion procedure 5 times was also treated in the same manner as the one described above to thereby give another test piece.

These test pieces thus obtained were subjected to a light-resistance test with the use of a high-pressure mercury lamp. Table 2 summarizes the results.

| [Composition] | part by weight |
|---|---|
| ethylene/propylene block copolymer | 100 |
| stearyl (3 5-di-tert-butyl-4- | 0.1 |
| hydroxyphenyl)propionate | |
| calcium stearate | 0.2 |
| dilauryl thiodipropionate | 0.2 |
| test compound (see Table 2) | 0.1 |

TABLE 2

| No. | Test compound | Light resistance (hr) Extruded once | Extruded 5 times |
|---|---|---|---|
| Comp. Ex. 2-1 | comp. cmpd. H-1 | 380$^{Hr}$ | 240$^{Hr}$ |
| Comp. Ex. 2-2 | comp. cmpd. H-2 | 400 | 250 |
| Ex. 2-1 | cmpd. No. 1 | 590 | 550 |
| Ex. 2-2 | cmpd. No. 2 | 600 | 560 |
| Ex. 2-3 | cmpd. No. 3 | 580 | 540 |
| Ex. 2-4 | cmpd. No. 4 | 590 | 540 |
| Ex. 2-5 | cmpd. No. 5 | 580 | 540 |
| Ex. 2-6 | cmpd. No. 6 | 580 | 540 |

EXAMPLE 3

A blend of the composition as specified below was milled and pressed to thereby give a sheet of 0.5 mm in thickness. The light resistance of this sheet was measured by using a Weather-O-meter and the brittle time was determined. Table 3 summarizes the results.

| [Composition] | part by weight |
|---|---|
| polyethylene | 100 |
| pentaerythritol tetrakis(3,5-di-tert-butyl-4-hydroxyphenyl-propionate) | 0.1 |
| calcium stearate | 1.0 |
| distearyl thiodipropionate | 0.3 |
| test compound (see Table 3) | 0.1 |

TABLE 3

| No. | Test compound | Light resistance (hr) |
|---|---|---|
| Comp. Ex. 3-1 | comp. cmpd. H-1 | 830$^{Hr}$ |
| Comp. Ex. 3-2 | comp. cmpd. H-2 | 980 |
| Ex. 3-1 | cmpd. No. 1 | 1100 |
| Ex. 3-2 | cmpd. No. 2 | 1130 |
| Ex. 3-3 | cmpd. No. 3 | 1090 |
| Ex. 3-4 | cmpd. No. 4 | 1080 |
| Ex. 3-5 | cmpd. No. 5 | 1100 |
| Ex. 3-6 | cmpd. No. 6 | 1090 |

EXAMPLE 4

A blend of the composition as specified below was roll-milled to thereby give a sheet of 1 mm in thickness. The light resistance of this sheet was measured in a Weather-O-meter. Table 4 summarizes the results.

| [Composition] | part by weight |
|---|---|
| polyvinyl chloride | 100 |
| dioctyl phthalate | 48 |
| epoxidized soybean oil | 2 |

| [Composition] | part by weight |
|---|---|
| tris(nonylphenyl) phosphite | 0.2 |
| calcium stearate | 1.0 |
| zinc stearate | 0.1 |
| test compound (see Table 4) | 0.1 |

TABLE 4

| No. | Test compound | Light resistance (hr) |
|---|---|---|
| Comp. Ex. 4-1 | comp. cmpd. H-1 | 330$^{Hr}$ |
| Comp. Ex. 4-2 | comp. cmpd. H-2 | 410 |
| Ex. 4-1 | cmpd. No. 1 | 630 |
| Ex. 4-2 | cmpd. No. 2 | 640 |
| Ex. 4-3 | cmpd. No. 3 | 610 |
| Ex. 4-4 | cmpd. No. 4 | 630 |
| Ex. 4-5 | cmpd. No. 5 | 620 |
| Ex. 4-6 | cmpd. No. 6 | 620 |

EXAMPLE 5

A blend of the composition as specified below was roll-milled and pressed to thereby give a sheet of 3 mm in thickness. The sheet was irradiated with light for 800 hours in a Weather-O-meter and then the tensile strength retention thereof was determined. Table 5 summarizes the results.

| [Composition] | part by weight |
|---|---|
| ABS resin | 100 |
| 4,4'-butylidenebis(2-tert-butyl-m-cresol) | 0.1 |
| test compound (see Table 5) | 0.2 |

TABLE 5

| No. | Test compound | Tensile strength retention (%) |
|---|---|---|
| Comp. Ex. 5-1 | comp. cmpd. H-1 | 54% |
| Comp. Ex. 5-2 | comp. cmpd. H-2 | 62 |
| Ex. 5-1 | cmpd. No. 1 | 86 |
| Ex. 5-2 | cmpd. No. 2 | 87 |
| Ex. 5-3 | cmpd. No. 3 | 84 |
| Ex. 5-4 | cmpd. No. 4 | 86 |
| Ex. 5-5 | cmpd. No. 5 | 86 |
| Ex. 5-6 | cmpd. No. 6 | 85 |

EXAMPLE 6

3,000 parts by weight of polypropylene glycol having a molecular weight of about 1,000 was vacuum-dried at 80° C. for 20 minutes. Then 135 parts by weight of tetramethylene glycol was added thereto and thoroughly mixed at 90° C. Next, 1,125 parts by weight of diphenylmethane 4,4'-diisocyanate was added thereto and milled under stirring for 10 minutes. The reaction product in the form of a mass was taken out, aged at 160° C. for 1 hour, cooled and then ground with a hammer to thereby give a thermoplastic polyurethane resin.

A blend of the composition as specified below was injection-molded by using a 3.5-oz in-line injection molding machine at a cylinder temperature of 170° to 190° C. Thus a test piece of 150 mm in length, 100 mm in width and 2 mm in thickness was formed. This test piece was irradiated with light in a fadeometer for 50 hours and then the elongation retention was measured. Table 6 summarizes the results.

| [Composition] | part by weight |
|---|---|
| thermoplastic polyurethane resin (the above-mentioned product) | 100 |
| ditridecyl pentaerythritol diphosphite | 0.2 |
| 2,6-di-tert-butyl-p-cresol | 0.1 |
| test compound (see Table 6) | 0.3 |

TABLE 6

| No. | Test compound | Elongation retention (%) |
|---|---|---|
| Comp. Ex. 6-1 | comp. cmpd. H-1 | 53% |
| Comp. Ex. 6-2 | comp. cmpd. H-2 | 66 |
| Ex. 6-1 | cmpd. No. 1 | 82 |
| Ex. 6-2 | cmpd. No. 2 | 84 |
| Ex. 6-3 | cmpd. No. 3 | 80 |
| Ex. 6-4 | cmpd. No. 4 | 81 |
| Ex. 6-5 | cmpd. No. 5 | 81 |
| Ex. 6-6 | cmpd. No. 6 | 82 |

As the results given in the above Tables 1 to 6 clearly show, when a cyanurate derivative of a polyamine having no ether bond in the molecule or a cyanurate derivative of a diamine having an ether bond in the molecule is used, not only an insufficient effect of improving the light-resistance of a polymeric material is achieved but also said effect is seriously deteriorated under severe conditions, for example, after extracting with hot water or repeatedly processing at a high temperature. In these cases, therefore, no satisfactory result can be obtained in practice.

In contrast thereto, it has been revealed that the polymeric material composition of the present invention obtained by adding a specific cyanurate compound derived from a tri- to hexa-valent polyamine having an ether bond to a polymeric material is highly excellent in the effect of improving the light-resistance of the polymeric material and said effect is scarcely deteriorated even under severe test conditions.

What is claimed is:

1. A piperidine compound represented by the following general formula (I):

$$A[(O-X)_n NH-Y]_m \qquad (I)$$

(wherein A represents a residue formed by eliminating m hydroxyl groups from a polyhydric (tri- to hexa-hydric) alcohol; X represents an alkylene group having 2 to 4 carbon atoms; n is an integer of from 1 to 15; m is an integer of from 3 to 6; and Y represents a group:

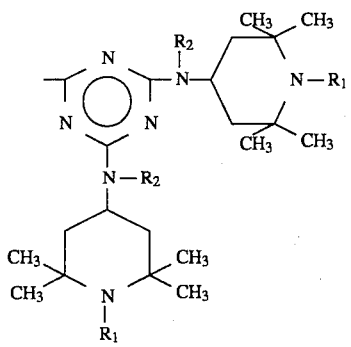

wherein $R_1$ represents a hydrogen atom, an alkyl, alkoxy or acyl group having 1 to 18 carbon atoms or an oxygen free radical; and $R_2$ represents a hydrogen atom or an alkyl group having 1 to 18 carbon atoms).

2. A piperidine compound as claimed in claim 1 wherein m in the above general formula (I) is 3.

3. A piperidine compound as claimed in claim 2 wherein A in the above general formula (I) is propanetriyl.

4. A piperidine compound as claimed in claim 1 wherein n in the above general formula (I) is from 1 to 3.

5. A piperidine compound as claimed in claim 1 wherein X in the above general formula (I) is propylene.

* * * * *